US012636142B2

(12) United States Patent
    Zhang

(10) Patent No.: US 12,636,142 B2
(45) Date of Patent: May 26, 2026

---

(54) STENT-GRAFT SYSTEM

(71) Applicant: HANGZHOU ENDONOM MEDTECH CO., LTD, Hangzhou (CN)

(72) Inventor: Wayne W Zhang, Hangzhou (CN)

(73) Assignee: Hangzhou EndoNom Medtech Co., Ltd, Hangzhou (CN)

( * ) Notice: Subject to any disclaimer, the term of this patent is extended or adjusted under 35 U.S.C. 154(b) by 559 days.

(21) Appl. No.: 18/133,425

(22) Filed: Apr. 11, 2023

(65) Prior Publication Data

US 2023/0248506 A1     Aug. 10, 2023

Related U.S. Application Data

(63) Continuation of application No. PCT/CN2021/123150, filed on Oct. 11, 2021.

(30) Foreign Application Priority Data

Oct. 13, 2020    (CN) .......................... 202011092050.9
Oct. 13, 2020    (CN) .......................... 202022275609.3

(51) Int. Cl.
    *A61F 2/07*                (2013.01)

(52) U.S. Cl.
    CPC .......... *A61F 2/07* (2013.01); *A61F 2002/072* (2013.01); *A61F 2002/077* (2013.01); *A61F 2250/0098* (2013.01)

(58) Field of Classification Search
    CPC .... A61F 2/07; A61F 2/82; A61F 2/852; A61F 2/856; A61F 2/89; A61F 2/90; A61F 2/91;

(Continued)

(56) References Cited

U.S. PATENT DOCUMENTS

| 8,105,372 | B1 * | 1/2012 | Chuter | ...................... | A61F 2/07 |
| | | | | | 623/1.13 |
| 2005/0102018 | A1 * | 5/2005 | Carpenter | ................. | A61F 2/07 |
| | | | | | 623/1.11 |

(Continued)

FOREIGN PATENT DOCUMENTS

| CN | 105832446 A | 8/2016 |
| CN | 109833116 A | 6/2019 |

(Continued)

OTHER PUBLICATIONS

Office Action Dated Aug. 19, 2024 for Corresponding European Application No. 21879346.1.

(Continued)

*Primary Examiner* — Robert A Lynch

(57) ABSTRACT

A stent-graft system (100) includes a mainbody stent-graft (1), an outer branch (2), and at least one inner branch (3, 4). The mainbody stent-graft (1) is a tubular structure with covering membrane (102) on a surface thereof, forming a radially recessed concave portion (103) thereon. The outer branch (2) extends outside the mainbody stent-graft (1), with one end attached to a side wall of the concave portion (103). The inner branch (3, 4) is attached to the inside wall of the mainbody stent-graft (1), with an outer opening (31, 41) on the side wall of the concave portion (103), wherein the outer opening (31, 41) is distal to the inner opening (21).

18 Claims, 8 Drawing Sheets

(58) Field of Classification Search
CPC ...... A61F 2/95; A61F 2/954; A61F 2002/061;
A61F 2002/065; A61F 2002/067; A61F
2002/072; A61F 2002/077; A61F
2002/075; A61F 2002/821; A61F
2002/828; A61F 2250/001; A61F
2250/0039; A61F 2250/006; A61F
2250/0098; A61F 2220/0075
See application file for complete search history.

(56) References Cited

U.S. PATENT DOCUMENTS

| | | | | |
|---|---|---|---|---|
| 2007/0168013 | A1* | 7/2007 | Douglas | A61F 2/07 623/1.35 |
| 2009/0048663 | A1* | 2/2009 | Greenberg | A61F 2/07 623/1.35 |
| 2013/0218257 | A1* | 8/2013 | Sun | A61F 2/07 623/1.36 |
| 2017/0086993 | A1 | 3/2017 | Roeder | |

FOREIGN PATENT DOCUMENTS

| | | |
|---|---|---|
| CN | 109875723 A | 6/2019 |
| WO | WO2020125226 A1 | 6/2020 |

OTHER PUBLICATIONS

International Search Report dated Jan. 21, 2022 for corresponding PCT Application No. PCT/CN2021/123150.
International Written Opinion dated Feb. 28, 2023 for corresponding PCT Application No. PCT/CN2021/123150.
Office Action Issued on Sep. 26, 2024 for Corresponding Chinese Patent Application No. 202011092050.9.
Office Action Issued on Aug. 17, 2025 for Corresponding Israel Patent Application No. 302050.

* cited by examiner proximal end ⟵⟶ distal end

1

STENT-GRAFT SYSTEM

CROSS-REFERENCE TO RELATED APPLICATIONS

The present application is a Continuation Application of PCT Application No. PCT/CN2021/123150, filed on Oct. 11, 2021, which claims the priority of Chinese Patent Application No. 202011092050.9 and Chinese Utility Model Application No. 202022275609.3, both filed on Oct. 13, 2020, the entire contents of which are hereby incorporated by reference.

TECHNICAL FIELD

The present disclosure relates to the technical field of medical devices, particularly to a stent-graft system.

DESCRIPTION OF THE PRIOR ART

Aortic aneurysm refers to the abnormal local or diffuse expansion of the aortic wall, which would result in rupture and compress surrounding organs and cause symptoms. Aortic aneurysm may occur in the ascending aorta, aortic arch, descending thoracic aorta, thoracoabdominal aorta, and abdominal aorta. Aortic aneurysms are classified into true aortic aneurysms, aortic pseudoaneurysms and dissecting aortic aneurysms according to the structures and etiologies.

Aortic aneurysm may gradually dilate and eventually rupture. The rupture risk is greatly related to the aneurysmal size. Embolism is another complication.

The dissecting aortic aneurysm occurs mainly due to focal damage of the arterial intima and high pressure blood causing a tear in the media (generally at an interface of the inner 1/3 and outer 2/3 of the media), which subsequently result in extensive separation between the inner and outer layers of aortic wall, generally forming two lumens. The original aortic lumen is called as true lumen, and the newly developed lumen following dissection is called as false lumen or pseudo-lumen.

Aortic diseases may involve branch arteries, and once the branch arteries are involved, it is difficult to be treated by endovascular technologies. At present, endovascular aortic repair, i.e., a minimally invasive method, has been developed, in which a stent-graft, namely arterial covered stent, can be inserted into the diseased aorta and through access vessel(s) to repair the pathologies while preserving blood supply. To build aortic stent-graft system, an arterial covered stent is compressed to an axial axis and loaded into a delivery device. During surgery the delivery system is inserted into aorta through femoral artery or iliac artery and then deployed at the pathological site(s). Branch covered stents can be placed through femoral or brachial artery. Once being deployed, the aortic stent-graft automatically returns to its original straight tubular shape and tightly attach to the aortic wall of the aorta to seal the aneurysm/pseudoaneurysm or dissection.

The current existing stent-grafts related to the treatments of aortic arch pathologies all have inevitable problems, causing the potential risk of complications during or after the procedures, which are specifically described as follows.

1. Chimney Stent

"Chimney" technique is also known as parallel stent technique, in which a stent is inserted in an occluded branch vessel and released in parallel with the main stent-graft in the aorta to achieve complete sealing of aneurysm or dissection with preservation of the arch branches. The chimney stents may be used for left subclavian artery, left carotid artery and/or brachiocephalic artery based on different aortic lesions. The chimney stents include "single-chimney", "double-chimney" and "triple-chimney" depending on the number of involved branch vessels. Advantages of the "chimney" technique include commonly used stent-grafts and covered stents which are widely available; and the technical difficulty is less challenging. However, the major concerns of "chimney" procedure are higher risk of endoleaks due to the gutter between the small stent and main aortic stent-graft; and the main aortic stent and the small stent are released in parallel fashion, the main stent-graft may compress the small stent, causing branch covered stent stenosis and occlusion.

2. Fenestrated Stent

The "fenestration" technique mainly involves in-situ fenestration, physician modified endograft (PMEG) fenestration or customized fenestration. In terms of in-situ fenestration, the main-body aortic stent-graft is positioned to seal the aortic lesion with coverage of the branches, and then aortic stent-graft is fenestrated using special instruments, such as puncture needle, hard-tip guide wire, laser or radio frequency catheter. The branch fenestration is then dilated and stented. However, the in-situ and PMEG fenestration procedures are off-label use with uncertain long-term outcomes. Customized branches stent-graft is made by manufacture according to individual patient's anatomy showed on the preoperative imaging studies. It can provide good long-term outcomes, but it is more expensive and need a certain period of time to produce, and is not available for emergent situation.

3. Integral Branched Stent

Integral branched stent-graft system can avoid the gutter leaks associated with chimney technique and provide better long-term durability than in-situ or PMEG fenestrations. Unfortunately, no aortic arch triple-branched stent-graft has been approved by Food and Drug Administration all over the world.

Therefore, there is a demand on developing an interventional stent-graft system suitable for both aneurysm and dissection with easier delivery and deployment, higher chance of complete sealing, lower complication rate and better long-term outcomes.

SUMMARY OF THE DISCLOSURE

Technical Problem

The objective of the present disclosure is to develop a novel stent-graft system with no need to be customized, which provides a widespread application and simplify surgical operations, particularly for aortic arch pathologies.

Technical Solution

To solve the above technical problems, the following technical solutions are adopted in the present disclosure. The stent-graft system includes a mainbody stent-graft, an outer branch, and at least one inner branch. The mainbody stent-graft is a tubular structure covered with membrane, forming a radially recessed concave portion thereon. The outer branch extends outside the mainbody stent-graft, and has one end connected to a side wall of the concave portion with an inner opening on the side wall of the concave portion. The inner branch is attached to an inside wall of the mainbody stent-graft, each of the at least one inner branch has one end connected to the side wall of the concave portion with an outer opening on the side wall of the concave portion.

Beneficial Effects

The stent-graft system of the present disclosure does not need to be customized. Its off-the-shelf advantages will provide simple procedure techniques for feasible clinical applications.

LIST OF REFERENCE NUMERALS

100/100a/100b/100c/100d/100e/100f, stent-graft system; 200, first branch covered stent; 300, second branch covered stent; 400, third branch covered stent; 600, aorta; 601, ascending aorta; 602, aortic arch; 603, descending aorta; 700, innominate artery; 800, left common carotid artery; 900, left subclavian artery;

1/1a/1c/1d/1e/1f, mainbody stent-graft; 101, support frame; 102/102c, covering membrane; 103, concave portion; 104, transition support frame; 105, last-releasing portion; 106, radiopaque marker; 11, proximal segment; 12, middle segment; 13, distal segment; 14, first transition segment; 15, second transition segment;

2/2a/2c/2d/2e/2f, outer branch; 21/21a/21f, inner opening; 22/22e/22f, membrane; 221f, flexible section; 23/23e/23f, support ring; 24, marker.

3/3a/3b/3c/3d/3e/3f, first inner branch; 31/31a/31c/31d, first outer opening; 32/32b, marker.

4/4a/4b/4c/4d/4e/4f, second inner branch; 41/41c/41d, second outer opening; 42/42b, marker.

DESCRIPTION OF EMBODIMENTS

Exemplary embodiments illustrating the features and advantages of the present disclosure will be described in detail hereinafter. It should be understood that various modifications of the present disclosure can be made in various embodiments, without departing from the scope of the present disclosure. The descriptions and accompanying drawings herein are provided substantially for illustration, but not restrictive to the present disclosure.

The present disclosure provides a stent-graft system, configured to be used for endovascular therapy of aortic arch pathologies. Using the covered stents, the blood flow channels between the aorta and three main branch arteries in aortic arch will be reconstructed and arch aneurysm or dissection will be sealed.

In the context, the term "proximal end" refers to an end adjacent to the heart in the direction of blood flow, and the term "distal end" refers to an end away from the heart, wherein the direction of blood flow in the artery flows from the proximal end to the distal end.

Referring to FIGS. 1 to 4, which show the structure and the use state of a stent-graft system 100 according to a first embodiment of the present disclosure.

Figure 1:
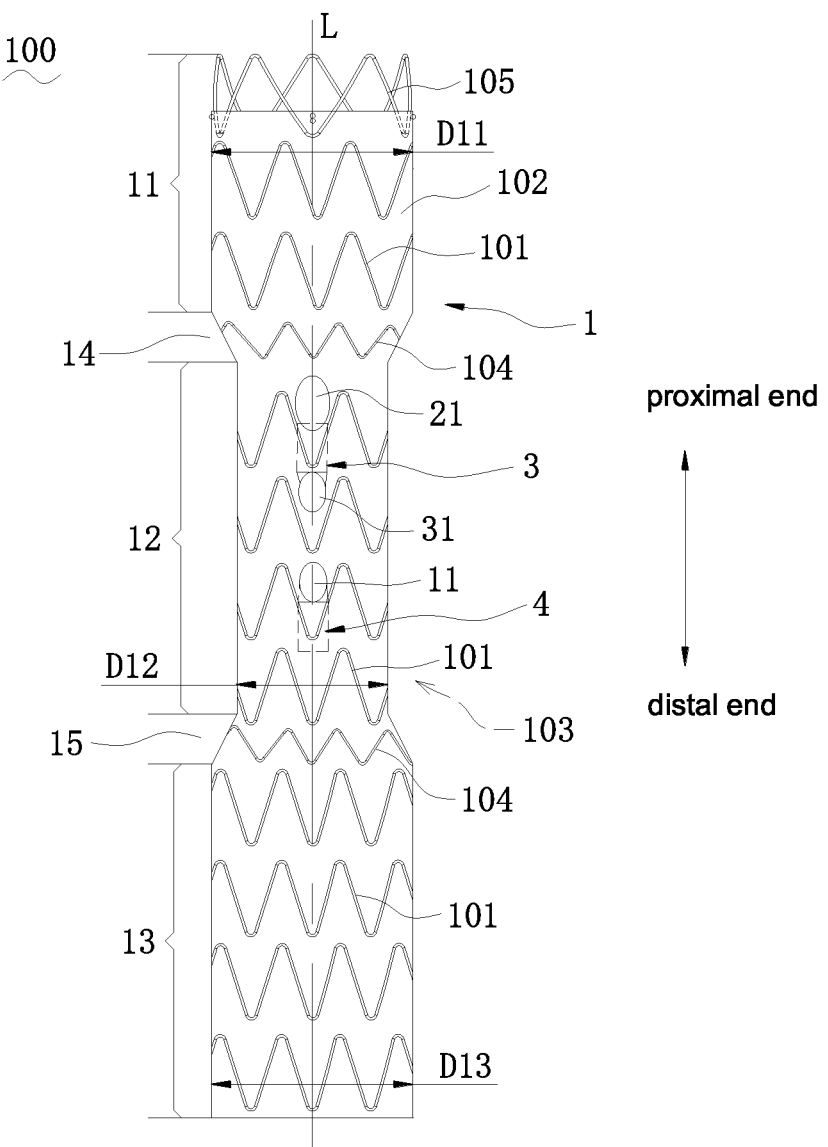
FIG. 1 is a schematic structural cranial view of a stent-graft system according to a first embodiment of the present disclosure.
Figure 2:
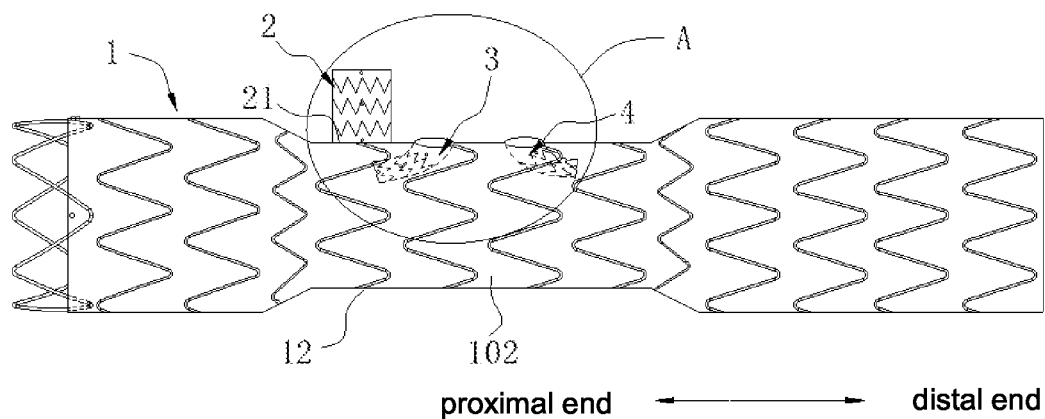
FIG. 2 is a schematic anterior view of the stent-graft system shown in FIG. 1.

Referring to FIGS. 1 and 2, the stent-graft system 100 according to this embodiment mainly includes a mainbody stent-graft 1, an outer branch 2 and two inner branches 3, 4, wherein the outer branch 2 and two inner branches 3, 4 are integrally connected to the mainbody stent-graft 1. The outer branch 2 protrudes outside the mainbody stent-graft 1, and the two inner branches 3, 4 are both located inside the mainbody stent-graft 1. The outer branch 2 and the two inner branches 3, 4 are arranged in sequence from the proximal end to the distal end, and fixedly connected to the mainbody stent-graft 1. For convenience of descriptions, the two inner branches 3, 4 are designated as a first inner branch 3 that is closer to the proximal end and a second inner branch 4 that is closer to the distal end of the mainbody stent-graft 1.

Referring mainly to FIG. 1, the mainbody stent-graft 1 is a tubular structure with a covering membrane 102 on the surface, and has a framework substantially composed of a plurality of ring-shaped support frames 101 arranged axially. The support frame 101 is a ring formed of an elastic rigid wire, and is radially collapsible or expandable.

The support frame 101 may be formed of a shape memory alloy material, preferably Nitinol material. The covering membrane 102 can be made from any material suitable for covering membrane, including but not limited to, low-porosity woven or knitted polyester, terylene materials, expanded polytetrafluoroethylene, polyurethane, silicone, ultra-high-molecular-weight polyethylene or other suitable materials.

Each support frame 101 is fixed to an inner or outer surface of the covering membrane 102, such that the covering membrane 102 is supported by the multiple support frames 101. Accordingly, the mainbody stent-graft 1 can expand and maintain as a tubular structure for blood to pass through. The support frames 101 are fixed to the covering membrane 102 by suturing or hot-pressing.

In an axial direction of the mainbody stent-graft 1 from the proximal end to the distal end, the mainbody stent-graft 1 has a proximal segment 11, a middle segment 12, and a distal segment 13 in sequence.

In this embodiment, each of the proximal segment 11, the middle segment 12 and the distal segment 13 is a tubular structure with substantially constant diameter. The diameter $D12$ of the middle segment 12 is smaller than the diameter $D11$ of the proximal segment 11 and the diameter $D13$ of the distal segment 13. Therefore, the entire mainbody stent-graft 1 is radially recessed at an outer periphery of the middle segment 12 to form a concave portion 103.

The diameter $D12$ of the middle segment 12 is substantially 70% to 80% of the diameter $D11$ of the proximal segment 11, and substantially 75% to 95% of the diameter D13 of the distal segment 13. The diameter D11 of the proximal segment 11 may be the same as or different from the diameter D13 of the distal segment 13.

In some embodiments, the mainbody stent-graft 1 further includes a first transition segment 14 located between the proximal segment 11 and the middle segment 12.

The first transition segment 14 is a tapered tubular structure with a diameter varying gradually. A proximal end of the first transition segment 14 is connected to the proximal segment 11, and a distal end of the first transition segment 14 is connected to the middle segment 12. Accordingly, the first transition segment 14 has a proximal diameter greater than its distal diameter.

In some embodiments, the main-body 1 further includes a second transition segment 15 located between the middle segment 12 and the distal segment 13.

The second transition segment 15 is tapered reversely as a tubular structure with a diameter varying gradually. A proximal end of the second transition segment 15 is connected to the middle segment 12, and a distal end of the second transition segment 15 is connected to the distal segment 13. Accordingly, the second transition segment 15 has a proximal diameter smaller than its distal diameter.

By means of the first transition segment 14 and the second transition segment 15, smooth transitional connections are formed respectively between the middle segment 12 and the proximal segment 11 and between the middle segment 12 and the distal segment 13, avoiding the risk of endoleak or local embolism caused by a locally formed groove-like dead structure due to abrupt change of the shape.

Each of the tubular segments 11, 12, 13, 14, and 15 of the mainbody stent-graft 1 is comprised of one or more support frames 101 and the covering membrane 102 attached to one or more support frames 101.

Particularly, the support frames 101 in the first transition segment 14 and the second transition segment 15 are defined as transition support frames 104. The transition support frames 104 are tapered to maintain truncated cone structures of the first transition segment 14 and the second transition segment 15. A smaller end surface of the transition support frame 104 faces the middle segment 12.

In this embodiment, both of the first transition segment 14 and the second transition segment 15 are supported with only one transition support frame 104. It can be understood that the number of the transition support frame 104 is not limited. If it is need, multiple transition support frames 104 can be added, and the multiple transition support frames 104 are tapered, and located on the same frustum surface.

Respective support frames 101 of the proximal segment 11, the middle segment 12 and the distal segment 13 are cylindrical, to maintain constant diameter of each segment 11, 12, and 13. A plurality of support frames 101 are provided at intervals in each of the tubular segments 11, 12, and 13, which gives the tubular segments 11, 12, and 13 all a good flexibility.

In some embodiments, the proximal segment 11 is also provided with a last-releasing portion 105, to release the proximal end of the stent-graft system 100 at the end of deployment. The last-releasing portion 105 is a radially collapsible ring structure, fixed to the covering membrane 102, and extended proximally beyond a proximal edge of the covering membrane 102. The structure of the last-releasing portion 105 may be the same as the structure of the support frame 101, but only part of the last-releasing portion 105 is covered by the covering membrane 102.

Further, the last-releasing portion 105 is further preferably provided with a protruding barb (not shown). A plurality of barbs that are arranged circumferentially may be provided. After the stent-graft system 100 is released, the barbs may hook up to the wall of blood vessel to increase the stability of the stent-graft system 100.

A plurality of radiopaque markers 106 are provided at a proximal end of the covering membrane 102 adjacent to or at the edge, for the purpose of well observing the position of the stent-graft system 100 where it is released during the operation. In this embodiment, the radiopaque markers 106 are arranged annually or along an 8-shaped structure, and fixed to the covering membrane 102 by suturing or hot-pressing. The radiopaque marker 106 is made of a radiopaque material, including but not limited to, gold, platinum, palladium, rhodium, tantalum, or alloys or composites of them. Taking platinum as an example, its alloy may be platinum-tungsten, platinum-iridium and the like.

Figure 3:
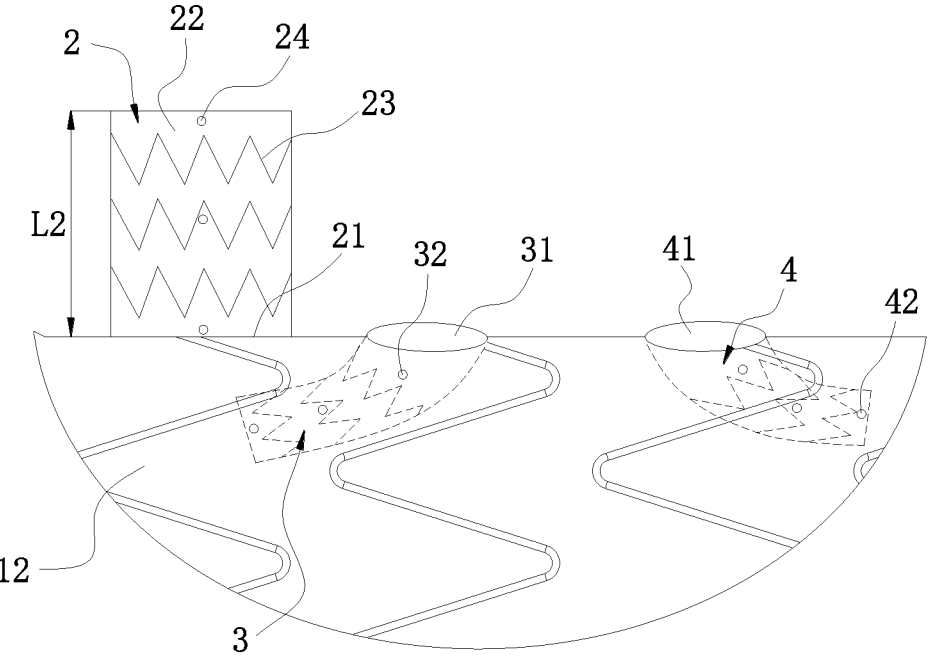
FIG. 3 is a partially enlarged view of proximal portion A of the stent-graft system shown in FIG. 2.

Referring to FIGS. 1 to 3, the outer branch 2 protrudes outside of the stent-graft system 1, and has one end connected to a side wall of the middle segment 12. The outer branch 2 has an inner opening 21 on the side wall of the middle segment 12, such that the inner lumens of the mainbody stent-graft 1 and the outer branch 2 are communicated through the inner opening 21. The outer branch 2 extends from the inner opening 21 in a direction away from the middle segment 12.

The outer branch 2 may be a tubular structure with unified diameter or variable diameter. In this embodiment, the outer branch 2 includes a tubular membrane 22 and a plurality of support rings 23 fixed to the surface of the membrane 22. The plurality of support rings 23 are arranged at intervals along an axial direction of the outer branch 2. Each support ring 23 may have the same structure as the support frame 101 of the mainbody stent-graft 1 and is also a radially collapsible and expandable ring structure. The membrane 22 can be formed of any suitable covering membrane material, including but not limited to, low-porosity woven or knitted polyester, terylene materials, expanded polytetrafluoroethylene, polyurethane, silicone, ultra-high-molecular-weight polyethylene or other suitable materials.

In other embodiments which are not shown, the outer branch 2 may be in the form of a bare stent, for example, a mesh-like bare stent.

The end of the outer branch 2 provided with the inner opening 21 is fixed to the covering membrane 102 of the middle segment 12 by suturing, and is integrated with the middle segment 12. The inner lumen of the outer branch 2 communicates with the inner lumen of the middle segment 12 at the inner opening 21. In practical production, a fenestration hole is made in the covering membrane 102 of the middle segment 12, and the outer branch 2 is sutured around the hole correspondingly.

The length L2 of the outer branch 2 is preferably 5 to 20 mm. When the stent-graft system 100 is released to a site requiring treatment, the outer branch 2 can be inserted and released into innominate artery. Since the innominate artery is the first branch (i.e., the proximal-most end) of the aortic arch, the position of the stent-graft system 100 can be well stabilized by engagement of the outer branch 2 into the innominate artery.

The outer branch 2 is preferably further provided with a marker 24. As shown in FIG. 3, the marker 24 is dot-like, and a plurality of markers are provided at intervals along the extension direction of the outer branch 2. Further, an outer periphery of the inner opening 21 may also be provided with a plurality of markers 24. The markers 24 are made of radiopaque material and fixed to the membrane 22 by suturing or hot-pressing. With the markers 24, the position of the outer branch 2 can be well visualized during operation, so that an external branch covered stent can be more quickly and precisely inserted into the innominate artery through the outer branch 2.

Referring to FIGS. 1 to 3 again, the first inner branch 3 is generally located inside the mainbody stent-graft 1, and attached to an inner wall of the middle segment 12. The first inner branch 3 has one end connected to the side wall of the middle segment 12 from inside. The end of the first inner branch 3 has a first outer opening 31 on the side wall of the middle segment 12. The outer opening 31 is distal to the inner opening 21 of the outer branch 2.

Similar to the outer branch 2, the first inner branch 3 is a tubular covered stent with constant diameter or variable diameter, and may be a bare stent or a stent with a membrane, which is not described in detail here. Similarly, a fenestration hole is made in the covering membrane 102 of the middle segment 12 corresponding to the first inner branch 3, and the end of the first inner branch 3 is sutured to the covering membrane 102 with the first outer opening 31 aligned with the fenestration hole of the covering membrane 102.

Except for the first outer opening 31, the remaining portion of the first inner branch 3 is located inside the middle segment 12, and can be fixed to the wall of the middle segment 12 from inside by suturing or bonding.

In some embodiments, the first inner branch 3 extends from its outer opening 31 towards the proximal end along the wall of the middle segment 12. In this embodiment, as shown in FIG. 1, the extension direction of the first inner branch 3 is substantially consistent with the axis L of the mainbody stent-graft 1.

In some embodiments, the first inner branch 3 is also provided with a plurality of markers 32 along its extension direction. Further, an outer periphery of the first outer opening 31 may also be provided with a plurality of markers 32, which are similar to the markers 24 on the outer branch 2, and will not be described here again.

Referring to FIGS. 1 to 3 again, the second inner branch 4 is distal to the first inner branch 3, and is also located inside the middle segment 12 and attached to the wall of the middle segment 12 from inside. The second inner branch 4 has a second outer opening 41 made on the superior side wall of the middle segment 12, and the second outer opening 41 is closer to the distal end than the first outer opening 31.

In this embodiment, the second inner branch 4 extends, from its outer opening 41 towards the distal end along the wall of the middle segment 12. The extension direction of the second inner branch 4 is opposite to the extension direction of the first inner branch 3, which allows the left subclavian artery covered stent to be inserted and deployed from femoral artery access or brachial artery access.

The second inner branch 4 is also provided with a plurality of markers 42 along its extension direction. Further, an outer periphery of the second outer opening 41 may also be provided with a plurality of markers 42. Other features of the second inner branch 4 may be referred to those of the first inner branch 3, and will not be repeated here again.

As shown in FIG. 1, the inner opening 21, the first outer opening 31 and the second outer opening 41 are substantially arranged at intervals on a same line parallel to the axis L of mainbody stent-graft 1. It can be understood that there are enough spaces among the three openings circumferentially.

Referring to FIGS. 1 to 3, in this embodiment, the first inner branch 3 and the second inner branch 4 are substantially symmetrically arranged.

Figure 4:
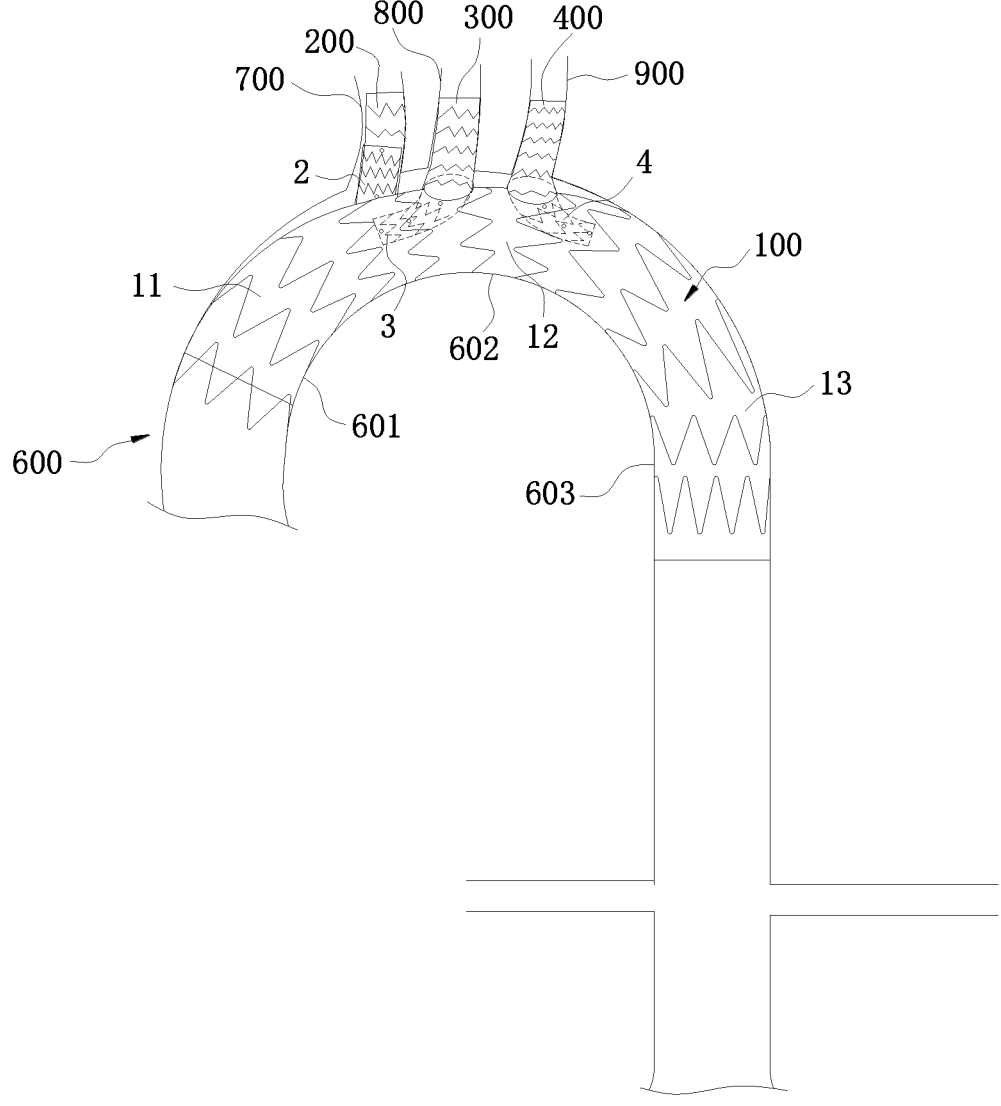
FIG. 4 shows the stent-graft system of FIG. 1 in use.

On the basis of the foregoing descriptions of the structure of the stent-graft system 100, and referring to FIG. 4, the stent-graft system 100 is delivered into the aorta 600 by a delivery system during endovascular repair of the aorta 600. The proximal segment 11 of the mainbody stent-graft 1 is inserted and deployed into the ascending aorta 601, which is attached against to the wall of the ascending aorta 601. The distal segment 13 is positioned in the descending thoracic aorta 603 and is attached against to the wall of the descending aorta 603. The middle segment 12 is located at the aortic arch 602 of the aorta 600. The outer branch 2 extends into an innominate artery 700 to facilitate the placement of the extension covered stent into distal innominate artery and help in stabilizing the position of the stent-graft system 100 in the aorta 600.

For the three branch blood vessels of the aortic arch 600, appropriate branch covered stents can be selected according to the sizes of the branch arteries, via the stent-graft system 100.

Specifically, a first branch covered stent 200 is deployed in and overlapped with the outer branch 2 for reconstruction of the innominate artery 700, to preserve the blood flow channel between aorta 600 and innominate artery 700. A second branch covered stent 300 extends out of the first inner branch 3 through the first outer opening 31 and then into the left common carotid artery 800, to reconstruct the blood flow channel between the aorta 600 and the left common carotid artery 800. A third branch covered stent 400 extends out of the second inner branch 4 through the second outer opening 41 and then into the left subclavian artery 900, to reconstruct the blood flow channel between aorta 600 and the left subclavian artery 900.

The exemplary implantation process of the stent-graft system 100 and the subsequent branch covered stents 200, 300, and 400 are described substantially as follows:

1. Releasing the proximal segment 11 of the stent-graft system 100 first;
2. Then releasing the proximal portion of the middle segment 12, wherein a pre-placed guidewire was previously inserted through the outer branch 2, when the pre-placed guidewire in the outer branch 2 is released, the guidewire is then inserted into or pulled by a snaring device into the innominate artery 700, via the outer branch 2;
3. Releasing the remaining portion of the mainbody stent-graft 1 rapidly, and finishing the last-releasing portion 105 of the proximal segment 11, to anchor the stent graft system 100 in aorta 600;
4. Reconstructing the three branch blood vessels including the innominate artery 700, the left common carotid artery 800, and the left subclavian artery 900 respectively in sequence with guidewire and catheter exchange techniques; releasing the branch covered stents 200, 300, and 400 of corresponding dimensions respectively; specifically, the first branch covered stent 200 is released in the outer branch 2 to reconstruct the innominate artery 700; the second branch covered stent 300 is released in the first inner branch 3 to reconstruct the left common carotid artery 800, and the third branch covered stent 400 is released in the second inner branch 4 to reconstruct the left subclavian artery 900.

As described above, in the stent-graft system 100 of this embodiment, the outer branch 2, the first inner branch 3 and the second inner branch 4 are integrally formed with the mainbody stent-graft 1. The branches 2, 3, and 4 can provide corresponding positioning and supporting functions to the three external branch covered stents 200, 300, and 400 respectively. Further, the branches 2, 3, and 4 are located at the middle segment 12 which has a smaller diameter than the proximal and distal segments 11, 13 of the mainbody stent-graft 1. Due to the formation of the concave portion 103 at the middle segment 12, a space between the concave portion 103 and the vascular wall of the aortic arch 602 allows to provide an enough room to manipulating guidewires and catheters during branch vessel selection. Therefore, the three external branch covered stents 200, 300, and 400 can be easily delivered into branch arteries during the operation for the reconstruction of the three main branches of arch aorta 600. Moreover, due to the smaller diameter of the middle segment 12, the stent-graft system 100 will not compress the branch covered stents to cause the stenosis and occlusion of branch covered stents 200, 300, and 400 following implantation. The branch covered stents 200, 300, and 400 are respectively anchored to the stent-graft system 100 by the outer branch 2, the first inner branch 3 and the second inner branch 4. The surgical operations are simpler, and the surgical procedure is shortened.

Particularly, among the branches 2, 3, and 4 of the stent-graft system 100, the most proximal outer branch 2 protrudes outside of the mainbody stent-graft 1. When the stent-graft system 100 is delivered to a preplanned site in aorta 600, the outer branch 2 can be placed into the innominate artery 700, facilitating confirming the stent-graft system 100 has been positioned in place. Following the deployments of the outer branch 2 and the mainbody stent-graft 1, the engagement of the outer branch 2 with the innominate artery 700 and the engagement of the mainbody stent-graft 1 with the aorta 600 will make the stent-graft system 100 as a whole unlikely to move. This facilitates the subsequent implantation of the branch covered stents. The two inner branches 3 and 4 distal to the outer branch 2 are located inside the mainbody stent-graft 1 with their outer openings 31, 41 exposed on the side wall of the mainbody stent-graft 1. With the operation space provided by the concave portion 103, larger position adjustment spaces are provided for covered stent insertion into the branch arteries via the inner branches 3 and 4 conveniently with no requirement to exactly align the openings of the inner branches 3, 4 with the orifices of the branch vessels. Therefore, the stent-graft system 100 has more widespread applicability and higher universality.

In addition, in this embodiment, the first inner branch 3 is designed as antegrade, in which the blood flow is in the same direction as in aorta 600, which is closer to normal anatomy.

The extension direction of the second inner branch 4 is aimed distally to ascending aorta, to avoid its inside entrance being blocked by the first inner branch 3 and give opportunities of cannulating left subclavian artery either from the left arm or femoral access.

Figure 5:
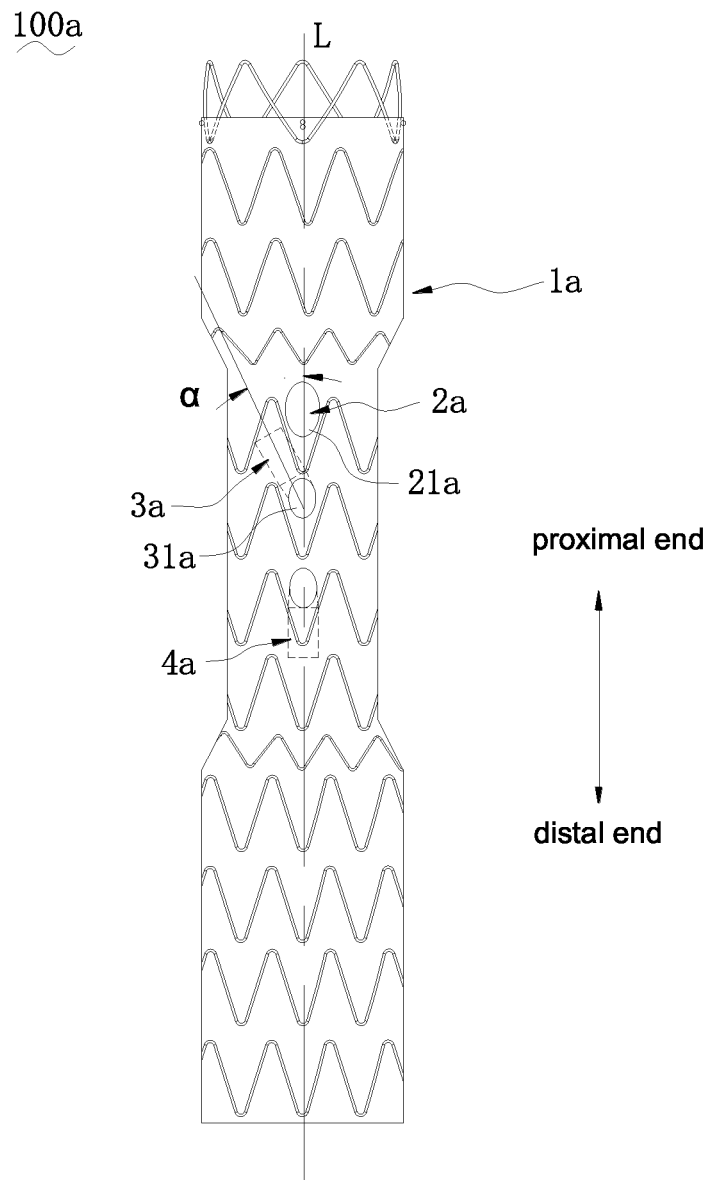
FIG. 5 is a schematic structural view of a stent-graft system according to a second embodiment of the present disclosure.

Referring to FIG. 5, which shows the structure of a stent-graft system 100a according to a second embodiment of the present disclosure.

The stent-graft system 100a of this embodiment is similar to the stent-graft system 100 of the first embodiment. For the same parts, references may be made to the above descriptions of the first embodiment, and the details will not be repeated here. This embodiment differs from the first embodiment in the extension direction of the first inner branch 3a.

As shown in FIG. 5, in this embodiment, the first inner branch 3a also extends from the first outer opening 31a towards the proximal end, however, the first inner branch 3a is slightly inclined toward to the anterior wall of the mainbody stent-graft 1a from its outer opening 31a, which gives a longer overlapping zone to the left common carotid covered stent.

Specifically, in this embodiment, the extension form of the first inner branch 3a in the mainbody stent-graft 1a may be substantially considered as the shape of a short segment of spiral line. An angle α is defined between the axis of the first inner branch 3a and the axis L of the mainbody stent-graft 1a, and the angle α is greater than 0 degree and less than 90 degrees.

Because of the oblique direction of the first inner branch 3a, it will not block the inner opening 21a of the outer branch 2a. Moreover, when a branch covered stent is implanted in the outer branch 2a, the branch covered stent would extend towards along the inner wall of the mainbody stent-graft 1a for a certain length to form an overlapping sealing zone. The design of the first inner branch 3a extending inclinedly to the axis L of the mainbody stent-graft 1a can prevent interferences between the branch covered stents implanted in the outer branch 2a and the first inner branch 3a.

The configuration and structures of the mainbody stent-graft 1a, the outer branch 2a and the second inner branch 4a in the stent-graft system 100a of this embodiment are the same as those in the first embodiment, and the details will not be repeated here.

Figure 6:
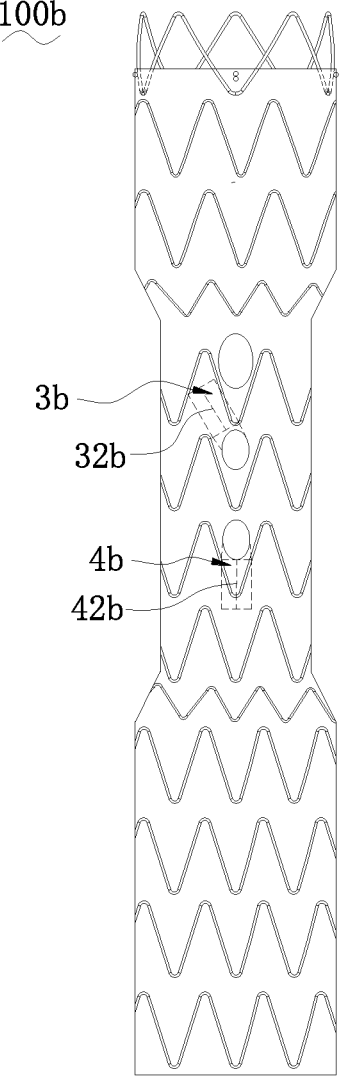
FIG. 6 is a schematic structural view of a stent-graft system according to a third embodiment of the present disclosure.

Referring to FIG. 6, which shows the structure of a stent-graft system 100b according to a third embodiment of the present disclosure.

The stent-graft system 100b of this embodiment is similar to the stent-graft system 100a of the second embodiment. For the same parts, references may be made to the above descriptions of the second embodiment and the first embodiment, and the details will not be repeated here. This embodiment differs from the second embodiment in that the marker 32b of the first inner branch 3b and the marker 42b of the second inner branch 4b are both strip-shaped.

As shown in FIG. 6, the first inner branch 3b is provided with a plurality of markers 32b, each of the markers 32b is strip-shaped, and the plurality of markers 32b are arranged in sequence along an axial direction of the first inner branch 3b, and arranged linearly as a whole. The extension direction of the first maker 32b is consistent with the overall extension direction of the multiple markers 32b. Specifically, a single marker 32b may be formed by a continuous radiopaque wire, or continuously wound on the metal frame of the first inner branch 3b.

The second inner branch 4b is provided with a plurality of markers 42b. Similarly, each of the marker 42b is strip-shaped, and the plurality of markers 42b are arranged in sequence along an axial direction of the second inner branch 4b, and arranged linearly as a whole. The extension direction of each of the marker 42b is consistent with the overall extension direction of the multiple markers 42b. Specifically, a single marker 42b may be formed by a continuous radiopaque wire, or continuously wound on the metal frame of the second inner branch 4b.

Compared with the dot-like markers 32, 42 in the first embodiment, the strip-shaped markers 32b, 42b in this embodiment are continuous. In the case where a plurality of markers are arranged with intervals along the axial direction of the inner branches 3b, 4b, the overall positions of the first inner branch 3b and the second inner branch 4b can be visualized more easily through the strip-shaped markers extending along the axial direction of the inner branches.

Figure 7:
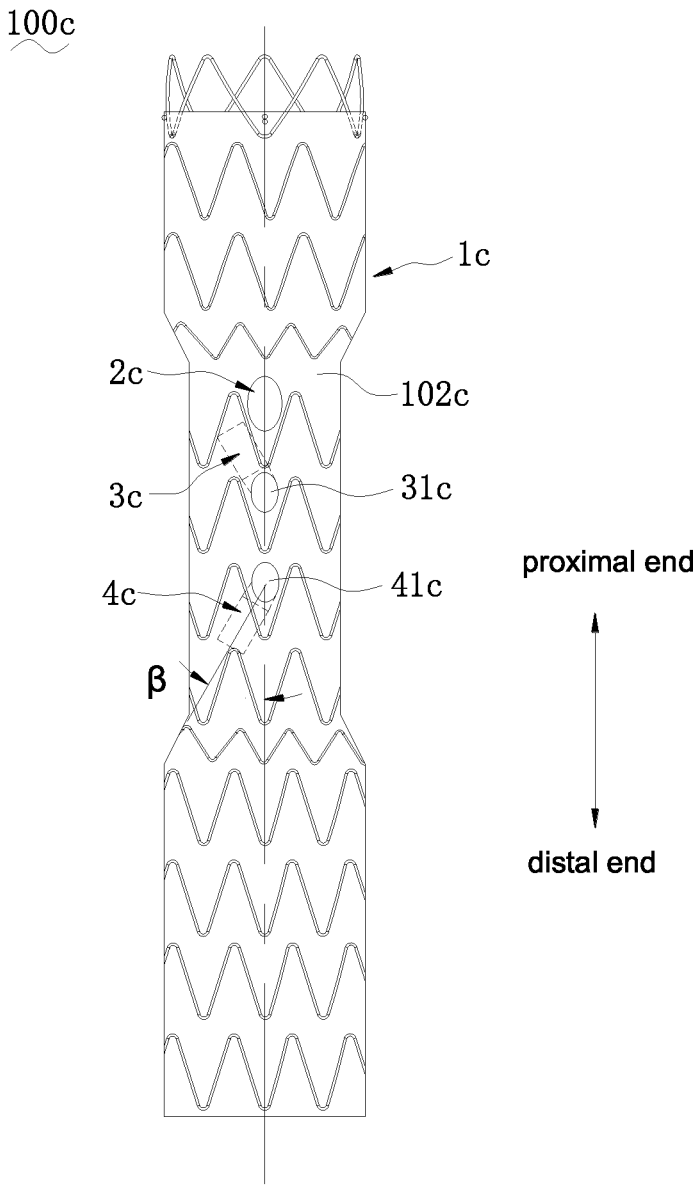
FIG. 7 is a schematic structural view of a stent-graft system according to a fourth embodiment of the present disclosure.

Referring to FIG. 7, which shows the structure of a stent-graft system 100*c* according to a fourth embodiment of the present disclosure.

The stent-graft system 100*c* of this embodiment is similar to the stent-graft system 100*a* of the second embodiment, but differs from the second embodiment in the extension direction of the second inner branch 4*c*.

As shown in FIG. 7, the second inner branch 4*c* also extends from the second outer opening 41*c* towards the distal end, however, the second inner branch 4*c* further extends in a circumferential direction of the mainbody stent-graft 1*c* from the second outer opening 41*c*. That is, the extension direction of the second inner branch 4*c* is inclined relative to the extension direction of the mainbody stent-graft 1*c*.

Specifically, in this embodiment, the extension form of the second inner branch 4*c* in the mainbody stent-graft 1*c* may also be substantially considered as the shape of a short segment of spiral line. An angle β is defined between the axis of the second inner branch 4*c* and the axis L of the mainbody stent-graft 1*c*, and the angle β is greater than 0 degree and less than 90 degrees.

Because of the extension manner of the second inner branch 4*c*, when the stent-graft system 100*c* is implanted into aorta, the second inner branch 4*c* can be located in the arch bending area of the aortic arch. The design of the second inner branch 4*c* extending inclinedly relative to the axis L of the mainbody stent-graft 1*c* can avoid the folding area of the covering membrane 102*c* due to bending, thereby preventing the entrance from being blocked by the covering membrane 102*c*.

In the structure shown in FIG. 7, a circumferential extension direction of the second inner branch 4*c* is the same as a circumferential extension direction of the first inner branch 3*c*. The second inner branch 4*c* and the first inner branch 3*c* are located on the same side of a line connecting the second outer opening 41*c* and the first outer opening 31*c*. In other embodiments not shown, the circumferential extension of the second inner branch 4*c* may be opposite to the circumferential extension direction of the first inner branch 3*c*.

The arrangements and structures of the mainbody stent-graft 1*c*, the outer branch 2*c* and the first inner branch 3*c* in the stent-graft system 100*c* of this embodiment are the same as those of the second embodiment, and the details will not be repeated here.

Figure 8:
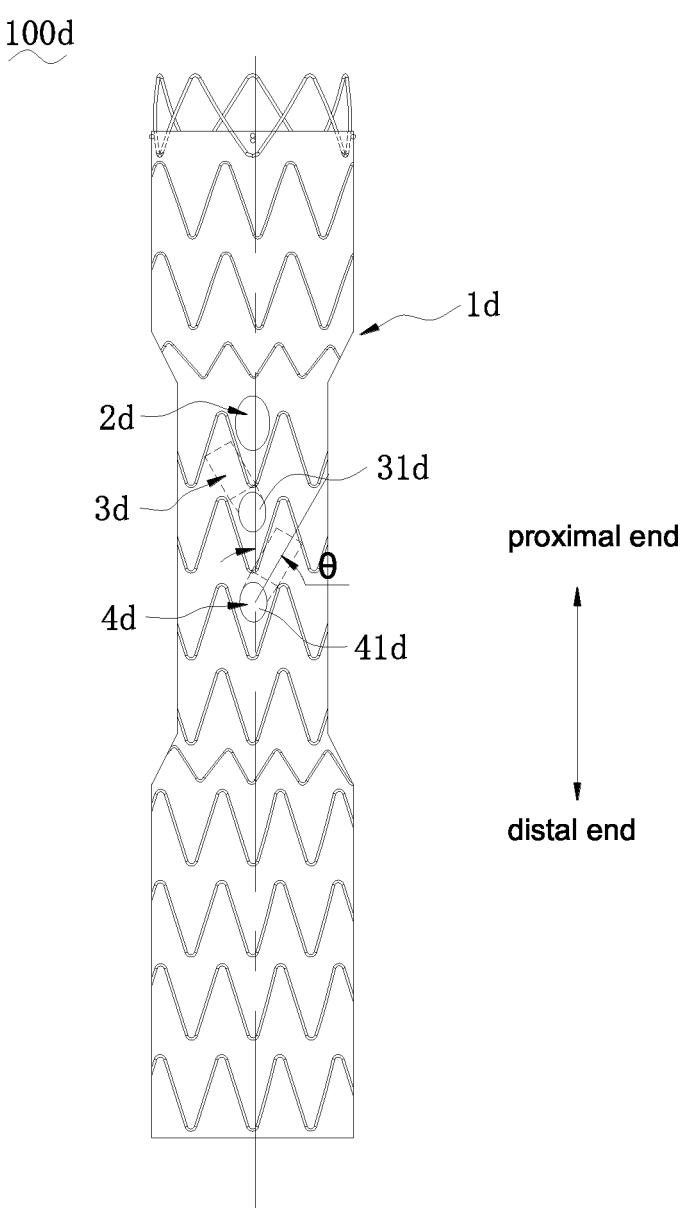
FIG. 8 is a schematic structural view of a stent-graft system according to a fifth embodiment of the present disclosure.

Referring to FIG. 8, which shows the structure of a stent-graft system 100*d* according to a fifth embodiment of the present disclosure.

The stent-graft system 100*d* of this embodiment is similar to the stent-graft system 100*a* of the second embodiment, and differs from the second embodiment in the extension direction of the second inner branch 4*d*.

As shown in FIG. 8, in this embodiment, the second inner branch 4*d* extends from the second outer opening 41*d* towards the proximal end, and the second inner branch 4*d* further extends in a circumferential direction of the mainbody stent-graft 1*d* from the second outer opening 41*d*. The extension direction of the second inner branch 4*d* is inclined relative to the extension direction of the mainbody stent-graft 1*d*.

Specifically, in this embodiment, the extension fashion of the second inner branch 4*d* in the mainbody stent-graft 1*d* may also be substantially considered as the shape of a short segment of spiral line. An angle θ is defined between the axis of the second inner branch 4*d* and the axis L of the mainbody stent-graft 1*d*, and the angle θ is greater than 0 degree and less than 90 degrees.

A circumferential extension direction of the second inner branch 4*d* is opposite to a circumferential extension direction of the first inner branch 3*d*. The second inner branch 4*d* and the first inner branch 3*d* are respectively located on two sides of a line connecting the first outer opening 31*d* and the second outer opening 41*d*. Taking the viewing direction in FIG. 8 as a reference, the first inner branch 3*d* extends leftwards, and the second inner branch 4*d* extends rightwards.

In this embodiment, the second inner branch 4*d* is also an antegrade branch, which is adapted to the blood flow direction. The second inner branch 4*d* and the first inner branch 3*d* both extend inclinedly, and their inclination directions are opposite and possible interferences between these two branches are avoided.

Figure 9:
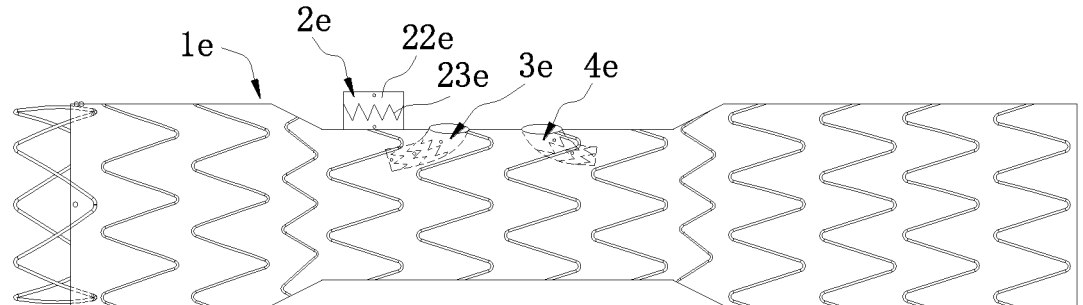
FIG. 9 is a schematic structural view of a stent-graft system according to a sixth embodiment of the present disclosure.

Referring to FIG. 9, which shows the structure of a stent-graft system 100*e* according to a sixth embodiment of the present disclosure.

The stent-graft system 100*e* of this embodiment is similar to the stent-graft system 100 of the first embodiment, but differs from the first embodiment in that the length of the outer branch 2*e* is shorter, which is about ⅓ to ½ of the length of the outer branch 2 in the first embodiment. Only one support ring 23*e* is provided on the membrane 22*e* of the outer branch 2*e*.

In this embodiment, a shorter outer branch 2*e* is provided, having increased flexibility to adapt different angles of between the branch covered stent and the stent-graft system. In this case, the shorter outer branch 2*e* may serve as a fixing end for the external branch covered stent, and the position of the innominate artery is not strictly limited.

The arrangements and structures of the mainbody stent-graft 1*e*, the first inner branch 3*e* and the second inner branch 4*e* in the stent-graft system 100*e* of this embodiment are the same as those of the first embodiment, and the details will not be repeated here.

Figure 10:
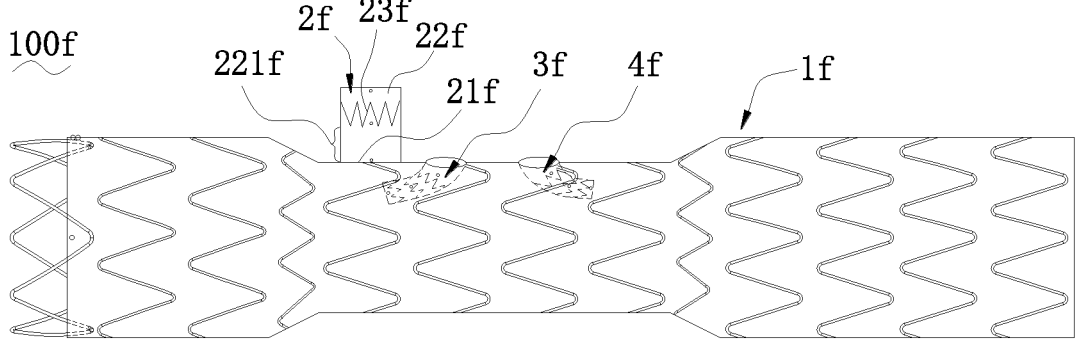
FIG. 10 is a schematic structural view of a covered stent according to a seventh embodiment of the present disclosure.

Referring to FIG. 10, which shows the structure of a stent-graft system 100*f* according to a seventh embodiment of the present disclosure.

The stent-graft system 100*f* of this embodiment is similar to the stent-graft system 100 of the first embodiment, but differs from the first embodiment in the structure of the outer branch 2*f*.

As shown in FIG. 10, in this embodiment, the outer branch 2*f* has a flexible section 221*f* capable of flexible deformation, and the flexible section 221*f* extends outwards from the inner opening 21*f*. The flexible section 221 is made of a flexible membrane material, which provides greater flexibility and is adapted to more patients with different anatomical structures. The length of the flexible section 221 is substantially 2 mm to 10 mm, and does not exceed ½ of the total length of the outer branch 2*f*.

The flexible section 221*f* may be formed by a section of the membrane 22*f* adjacent to the mainbody stent-g raft 1*f* without support ring 23*f* provided thereon. That is, the support ring 23*f* is not arranged in a section of the membrane 22*f* of the outer branch 2*f* with a length ranging from about 2 mm to 10 mm from the inner opening 21*f*. The section of the membrane 22*f* without support ring 23*f* provided thereon constitutes the flexible section 221*f*. The remaining part of the membrane 22*f* other than the flexible section 221*f* is provided with the support ring 23*f* to maintain the outer branch 2*f* tubular. The diameters of inner opening 21*f* and the support ring 23*f* are equal, but the flexible section 221*f* has a diameter that is 1-2 mm smaller than those of the inner opening 21*f* and the support ring 23*f*. If needed, the outer branch 2*f* can be pushed or pulled into the stent-graft system 100f and converted to an inner branch. This configuration will make the stent-graft system 100f suitable for aortic arch aneurysm, dissection with small lumen, and other pathologies.

The arrangements and structures of the mainbody stent-graft 1f, the first inner branch 3f and the second inner branch 4f in the stent-graft system 100f of this embodiment are the same as those of the first embodiment, and the details will not be repeated here.

In the above embodiments, all the examples with two inner branches provided on the mainbody stent-graft are taken for illustration, and in combination with arrangement of the outer branch, the three branch artery vessels of the aorta can be reconstructed. However, it can be understood that in some embodiments not shown, the number of inner branches may be decreased to one for the cases in whom two branch arteries need to be reconstructed.

As can be known from the detailed descriptions of the above embodiments, by using the covered stent of the present disclosure, the aortic stent-graft system and the external branch artery covered stents may be independent structures, to adapt to various normal and abnormal anatomies. The aortic stent-graft system and branch artery covered stents will be off-the-shelf and can be appropriately selected according to the specific conditions of the pathology and the sizes of the vessels, by which the customization of aortic arch stent-graft systems is not needed. Therefore, this aortic arch stent-graft system will be available for both elective and emergent situations.

Although the present disclosure has been described with reference to several exemplary embodiments, it should be understood that the terms used are illustrative and exemplary only, with no intend to limit the present disclosure. As the present disclosure can be implemented in various ways without departing from the spirit or essence of the present disclosure, it should be understood that the above embodiments are not limited to any of the foregoing details, and shall be interpreted broadly within the spirit and scope defined by the appended claims. Therefore, all changes and modifications falling within the scope of claims or their equivalents shall be covered by the appended claims.

The invention claimed is:

1. A stent-graft system, comprising:
   a mainbody stent-graft being of a tubular structure with a covering membrane on a surface thereof, and forming a radially recessed concave portion thereon;
   an outer branch extending outside the mainbody stent-graft, having one end connected to a side wall of the concave portion with an inner opening on the side wall of the concave portion; and
   at least one inner branch, attached to an inside wall of the mainbody stent-graft, each of the at least one inner branch having one end connected to the side wall of the concave portion with an outer opening on the side wall of the concave portion,
   wherein the outer branch has a flexible section which extends outwards from the inner opening; and
   wherein a length of the flexible section is 2 mm to 10 mm, without exceeding ½ of a total length of the outer branch.

2. The stent-graft system according to claim 1, wherein the at least one inner branch comprises two inner branches, which are a first inner branch and a second inner branch respectively, wherein the first inner branch has a first outer opening on the side wall of the concave portion, the second inner branch has a second outer opening on the side wall of the concave portion, and the second outer opening is distal to the first outer opening.

3. The stent-graft system according to claim 2, wherein the first inner branch extends from the first outer opening towards a proximal end.

4. The stent-graft system according to claim 3, wherein the second inner branch extends from the second outer opening towards a distal end.

5. The stent-graft system according to claim 4, wherein with extension towards the distal end, the second inner branch further extends in a circumferential direction of the mainbody stent-graft from the second outer opening.

6. The stent-graft system according to claim 3, wherein with extension towards the proximal end, the first inner branch further extends in a circumferential direction of the mainbody stent-graft from the first outer opening.

7. The stent-graft system according to claim 6, wherein the second inner branch extends from the second outer opening towards the proximal end, and with extension towards the proximal end, the second inner branch further extends in the circumferential direction of the mainbody stent-graft from the second outer opening; and a circumferential extension direction of the second inner branch is opposite to a circumferential extension direction of the first inner branch.

8. The stent-graft system according to claim 1, wherein a length of the outer branch is 5 mm to 20 mm.

9. The stent-graft system according to claim 1, wherein the flexible section is made of a flexible membrane material.

10. The stent-graft system according to of claim 1, wherein each of the outer branch and the inner branch is marked with a marker, and the marker is made of radiopaque material.

11. The stent-graft system according to claim 10, wherein the marker is circumferentially arranged at the inner opening or the outer opening.

12. The stent-graft system according to claim 10, wherein the outer branch or the at least one inner branch is provided with the marker along an extension direction thereof.

13. The stent-graft system according to claim 10, wherein the marker is hot pressed or sutured on the outer branch and the inner branch.

14. The stent-graft system according to claim 1, wherein the mainbody stent-graft comprises a proximal segment, a middle segment, and a distal segment in sequence from a proximal end to a distal end; a diameter of the middle segment is less than a diameter of the proximal segment and a diameter of the distal segment because of the concave portion of the mainbody stent-graft.

15. The stent-graft system according to claim 14, wherein two ends of the middle segments are respectively connected to the proximal segment and the distal segment by two transition segments; and each of the transition segments has a tapered transition support frame supporting the covering membrane.

16. The stent-graft system according to claim 14, wherein the proximal segment is provided with a last-releasing portion that is a radially collapsible ring structure fixed to the covering membrane, and extending beyond a proximal edge of the covering membrane.

17. The stent-graft system according to claim 16, wherein the last-releasing portion is provided with barbs arranged circumferentially.

18. The stent-graft system according to claim 1, wherein a radiopaque marker is provided at an end of the covering membrane, and the radiopaque marker is made of radiopaque material.

* * * * *